(12) United States Patent
Zhou et al.

(10) Patent No.: US 9,456,802 B2
(45) Date of Patent: Oct. 4, 2016

(54) MECHANICAL SCANNING ULTRASOUND TRANSDUCER WITH MICROMOTOR

(71) Applicant: Muffin Incorporated, West Lafayette, IN (US)

(72) Inventors: Yun Zhou, West Lafayette, IN (US); Peter S. McKinnis, West Lafayette, IN (US); Neal E. Fearnot, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 50 days.

(21) Appl. No.: 14/051,812

(22) Filed: Oct. 11, 2013

(65) Prior Publication Data

US 2014/0107492 A1    Apr. 17, 2014

Related U.S. Application Data

(60) Provisional application No. 61/713,186, filed on Oct. 12, 2012.

(51) Int. Cl.
*A61B 8/12* (2006.01)
*A61B 8/00* (2006.01)
*G10K 11/35* (2006.01)
*G01S 15/89* (2006.01)
*A61B 8/08* (2006.01)

(52) U.S. Cl.
CPC .............. *A61B 8/4461* (2013.01); *A61B 8/12* (2013.01); *A61B 8/445* (2013.01); *A61B 8/4483* (2013.01); *G01S 15/8943* (2013.01); *G10K 11/357* (2013.01); *A61B 8/4494* (2013.01); *A61B 8/483* (2013.01)

(58) Field of Classification Search
CPC .................... G10K 11/357; G01S 15/8943
See application file for complete search history.

(56) References Cited

U.S. PATENT DOCUMENTS 4,785,816 A    11/1988 Dow et al.
5,176,141 A *   1/1993 Bom .................. A61B 8/12
                                                 600/467

(Continued)

FOREIGN PATENT DOCUMENTS

JP      2004/129697        4/2004
WO      WO 2012/061643 A1  5/2012

OTHER PUBLICATIONS

International Search Report and Written Opinion issued in PCT/US2013/064570, dated Jan. 24, 2014.

(Continued)

*Primary Examiner* — Long V Le
*Assistant Examiner* — Colin T Sakamoto
(74) *Attorney, Agent, or Firm* — Woodard, Emhardt, Moriarty, McNett & Henry LLP

(57) ABSTRACT

A system for use with ultrasound procedures including an ultrasound control and/or imaging system which has a microminiature motor, a rotatable reflector and a stationary ultrasound transducer. The transducer may be placed between the motor and the reflector, so as to eliminate the need for placement of wires or other artifact-creating items in the path of ultrasound signals. In particular embodiments, such systems can be incorporated in or retrofitted to commercially standard diagnostic and therapeutic catheters or other housings. Examples can be used in variety of ultrasound procedures, e.g. to perform intravascular ultrasound (IVUS) imaging.

23 Claims, 2 Drawing Sheets

(56) References Cited

U.S. PATENT DOCUMENTS

| | | | |
|---|---|---|---|
| 5,240,003 A * | 8/1993 | Lancee | A61B 8/12 310/162 |
| 5,373,845 A | 12/1994 | Gardineer et al. | |
| 5,507,294 A * | 4/1996 | Lum | A61B 8/06 600/459 |
| 6,371,915 B1 | 4/2002 | Koger et al. | |
| 8,206,307 B2 | 6/2012 | Barnard et al. | |
| 2002/0082503 A1 | 6/2002 | Chandrasekaran et al. | |
| 2002/0087083 A1 | 7/2002 | Nix et al. | |
| 2002/0143252 A1 | 10/2002 | Dunne et al. | |
| 2006/0030797 A1 | 2/2006 | Zhou et al. | |
| 2006/0173348 A1 | 8/2006 | Wilser et al. | |
| 2007/0038114 A1 | 2/2007 | Couvillon, Jr. | |
| 2007/0149917 A1 | 6/2007 | Bennett et al. | |
| 2008/0097403 A1 | 4/2008 | Donaldson et al. | |
| 2008/0177138 A1 | 7/2008 | Courtney et al. | |
| 2008/0221506 A1 | 9/2008 | Rodriguez et al. | |
| 2009/0306518 A1 | 12/2009 | Kurse et al. | |
| 2010/0036258 A1 | 2/2010 | Dietz et al. | |
| 2010/0160788 A1 | 6/2010 | Davies et al. | |
| 2010/0234736 A1 | 9/2010 | Corl | |
| 2010/0249602 A1 | 9/2010 | Buckley et al. | |
| 2010/0249604 A1 | 9/2010 | Hastings et al. | |
| 2011/0021924 A1 | 1/2011 | Sethuraman et al. | |
| 2011/0071401 A1 | 3/2011 | Hastings et al. | |
| 2011/0196286 A1 | 8/2011 | Robertson et al. | |
| 2011/0263986 A1 | 10/2011 | Park et al. | |
| 2011/0301508 A1 | 12/2011 | Sethuraman et al. | |
| 2012/0022379 A1 * | 1/2012 | Gubbini et al. | 600/461 |
| 2012/0172698 A1 | 7/2012 | Teo et al. | |

OTHER PUBLICATIONS

International Search Report and Written Opinion issued in PCT/US2013/064579, dated Jan. 23, 2014.

International Search Report and Written Opinion issued in PCT/US2013/064606, mailed Jan. 8, 2014.

International Search Report and Written Opinion issued in PCT/US2013/064611, dated Jan. 28, 2014.

International Search Report and Written Opinion issued in PCT/US2013/064618, dated Jan. 24, 2014.

* cited by examiner

MECHANICAL SCANNING ULTRASOUND TRANSDUCER WITH MICROMOTOR

CROSS-REFERENCE TO RELATED APPLICATION

This application claims the benefit of U.S. Provisional Application No. 61/713,186 filed Oct. 12, 2012, which is hereby incorporated by reference.

BACKGROUND

Intravascular ultrasound (IVUS) allows the use of ultrasound technology to gather images from within portions of a body. In recent years, IVUS technology has provided physicians with the ability to obtain important diagnostic information that is not available from traditional x-ray techniques or other ultrasound techniques, thereby increasing the effectiveness of diagnosis and treatment. For example, IVUS can help to determine plaque volume and the degree of stenosis within an artery lumen. That information is often difficult to obtain through angiographic imaging and exterior ultrasound imaging, particularly in regions having multiple overlapping arterial segments.

One type of ultrasound transducer includes a stationary ultrasound array which can image the full slice of the body tissue due to the particular positioning of the ultrasound elements in the array. Other configurations include a single, rotating ultrasound element, which obtains imaging data by mechanically rotating the ultrasound element during imaging. In that case, a cross-sectional image of the body tissue is obtained by the ultrasound element emitting sequential ultrasound pulses at changing rotational positions. Advantages of the single-element rotational design when compared to an array design include smaller size, better image quality, possible higher center frequency, lower cost for the ultrasound imaging console, and less ring down artifacts (dead zone).

Single element designs can also include certain disadvantages, such as non-uniform rotational distortion (NURD). During imaging procedures including a single element design, the ultrasound element is typically rotated with a torque cable. Ultrasound pulses are emitted in an even-spaced time-sequential manner under the expectation of a uniform rotation rate of the ultrasound element. Each reflected ultrasound pulse represents a portion of a cross-sectional image. An image processor assembles the data based on the assumption that the data points represent images from evenly-spaced pulses. However, it can be difficult to achieve a uniform rotation rate for the ultrasound element when using a torque cable as a driving means. The ultrasound element can be one to two meters from the driving end of the torque cable. The torque cable must follow all the bends along the path of a blood vessel to reach the region to be imaged and there can be a lag (a delay in transfer) in the rotation of the torque cable from the handle end to the distal or operational end which causes the ultrasound element to rotate at a non-uniform rate even when the rotation source rotates at a uniform rate. The non-uniform rate causes the resulting images to be distorted.

Other problems exist in current designs. Typically, IVUS elements are mounted to a dedicated catheter. The IVUS catheter usually shares the same utility lumen as other therapeutic catheters preventing a physician from performing IVUS imaging monitoring simultaneously with or during a single procedure with other intravascular procedures, such as, for example, deploying a stent or graft or performing a biopsy.

Attempts to create single element IVUS imaging systems without torque cables present further problems. Current commercialized designs use costly rotary transformers to connect stationary electrical wires from a console to a rotating ultrasound transducer. However, the rotary transformer is among the most expensive parts of a mechanical scanning IVUS catheter. Alternative designs place a rotary transformer on a console (proximal) side of the reflector. However, the cost of the coaxial connector that couples both mechanical movement and an electrical signal is comparable to the cost of the rotary transformer, further increasing overall cost.

Thus, there is a need to have an ultrasound emission design that could be integrated to a general catheter or other device for internal use in a patient, that is cost effective, and which produces images free from NURD artifacts.

SUMMARY

Among other things, there are disclosed embodiments of a system for use with ultrasound procedures including an ultrasound control or imaging system which has a microminiature motor, a rotatable reflector and a stationary ultrasound transducer which is mountable to or incorporated in internal medical devices such as commercially standard diagnostic and therapeutic catheters, and in particular examples can perform two-dimensional (2D) IVUS imaging.

In particular embodiments, the system is a stand alone device which is configured to be adaptable to existing medical devices such as catheters and other devices which are used internally (e.g. intravascularly, per- or subcutaneously, or through insertion into a bodily orifice). The reflector is positioned distally relative to the transducer and is connected to a rotary shaft of the microminiature motor. The transducer is connected to a support which is positioned concentric relative to the shaft of the motor. The housing of the microminiature motor is connected to a housing of the system. The support of the ultrasound element is also connected to the housing of the system. In that way the reflector is rotatable about an axis while the transducer remains stationary relative to the housing.

The system is capable of creating an image as a two-dimensional slice, a cone shape slice, or a toroidal section shape of a portion of body tissue. The image is obtained through use of a single element ultrasound transducer which emits an ultrasound signal along the axial direction of the ultrasound transducer. The reflector reflects the ultrasound signal in a direction non-parallel, and in particular embodiments perpendicular, to the ultrasound transducer axial direction. As the reflector rotates through a 360 degree arc, an image is created of a section of body tissue.

Embodiments of the ultrasound element can include wire (s) configured to run along or through the support. Because the reflector is located distally relative to the ultrasound element and the wires connecting the ultrasound element run towards an ultrasound system console or proximal end of the system, the imaging plane is free from any wires which would otherwise cross the imaging plane and create an artifact or blocked portion of the ultrasound image.

The system is configured, in some embodiments, to be attachable to existing medical devices, such as, for example, a catheter. The system may be placed within an existing lumen or alternatively could be attached externally to a medical device. Wires connecting the ultrasound element and the microminiature motor could be routed through a dedicated lumen which can be attached externally to a medical device or alternatively it could be routed within the medical device such as through an existing lumen within a catheter.

In specific embodiments, a system for use with ultrasound procedures includes an ultrasound element connected to a support for maintaining the transducer in position, the transducer adapted to emit and receive ultrasound signals substantially along an axis, and a reflector connected to a shaft, the reflector positioned with respect to the ultrasound element to reflect in a direction non-parallel to the axis ultrasound waves emitted from the transducer. The shaft and support are positioned concentrically and the shaft is rotatable relative to the support about the axis. A housing around the transducer and the reflector may be provided, with the support fixed in a stationary position relative to the housing. At least one electrical wire may be connected to the transducer, with the reflector angled with respect to the axis of the transducer so that a reflection direction from the reflector is non-parallel to the axis, and so that the wire does not cross the reflection direction. Particular embodiments have a reflector that forms an angle between 10 and 84 degrees with respect to the axis.

Examples of a microminiature motor rotatably connected to the shaft include a piezoelectric or electromagnetic motor. Part of the support for the transducer may be positioned concentrically inward relative to the motor, and the motor, reflector, and transducer are configured to be positioned in a medical device, and configured for internal use (e.g. sized and configured for intravascular usage). One or more electrical wires connected to the transducer and one or more electrical wires connected to the microminiature motor are provided in specific embodiments, for example wherein at least one electrical wire is housed within the support. A housing containing the reflector and transducer may be provided, with the housing having a leading end, and wherein the reflector is positioned between the leading end and the transducer. An example of a transducer is a single element transducer.

In further examples, an internal ultrasound system includes a transducer connected to a support, a reflector positioned distally of the ultrasound element to reflect a signal from the ultrasound element, the reflector connected to a shaft, and a microminiature motor connected to the shaft and configured to cause the shaft to rotate. The motor, reflector, and transducer are configured to be positioned in a medical device having a leading end and adapted for internal medical use, and wherein the reflector is closer to the leading end than the transducer is to the leading end. The motor may be a piezoelectric or an electromagnetic motor, as noted above, with a size of approximately 0.3 mm to 4 mm. The shaft and support can be positioned concentrically, and the shaft may be rotatable about an axis relative to the support. A housing may be provided so that the support is fixed in a stationary position relative to the housing. Particular embodiments include the support being positioned concentrically inward relative to the motor, and/or the use of a single element transducer. One or more electrical wires may be connected to the transducer and one or more electrical wires may be connected to the motor, for example with at least one electrical wire housed within the support. The shaft is rotatable about an axis coaxial with the support in some embodiments, with the reflector generating a viewing angle approximately perpendicular to the axis, and at each angular position of the reflector the viewing angle does not cross any electrical conductors.

Embodiments of ultrasound systems may have a motor with a drive shaft, a stationary transducer positioned coaxially with the motor and configured to emit and receive ultrasound signals, and a mirror positioned to reflect an ultrasound signal between the transducer and a viewing window and operatively disposed to rotate in response to with the drive shaft. The viewing window is free from any echo-opaque members (i.e. members having an acoustic impedance such that all or a substantial fraction of ultrasound striking them will be reflected).

The system described herein can be used with existing ultrasound imaging equipment and procedures. For example, the system can be used with an ultrasound imaging system which includes a console portion having a user interface and controls for a physician as well as a display for displaying an ultrasound image. The console portion can be connected to commercially available ultrasound probes or catheters with compatible pinout or other medical devices which are configured for internal procedures. The system as described herein can be attached to a catheter or other medical device such that ultrasound procedures can be performed simultaneously or sequentially with other procedures. Accordingly, the system described herein will allow a physician to retrofit existing medical devices such as catheters or biopsy needles with an ultrasound system such that ultrasound procedures can be performed simultaneously along with other medical procedures such as deploying a stent or graft obtaining a biopsy sample, tissue resection, making or closing holes in tissue, ablation, cauterizing, stone removal, drug delivery, cell delivery, filter delivery, lasing, aspiration, device deployment or removal, stimulation of tissue, lavage, fluid drainage, centesis, treating conditions such as pneumothorax, PCI, or thrombolysis, and other medical procedures.

Further forms, objects, features, aspects, benefits, advantages, and embodiments of the present disclosure will become apparent from a detailed description and drawings provided herewith.

DESCRIPTION OF THE SELECTED EMBODIMENTS

Figure 1:
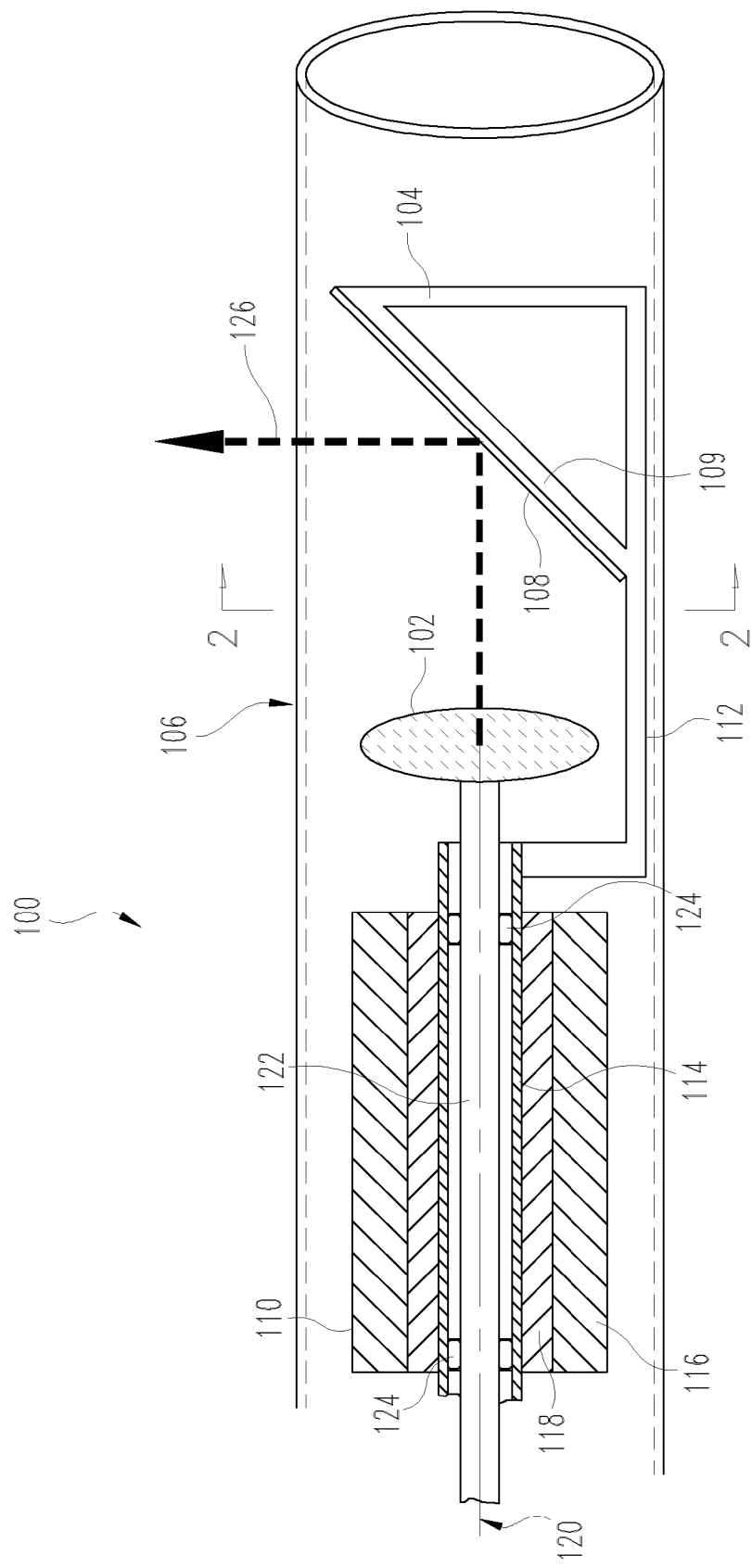
FIG. 1 is a partial cross-sectional illustrative view of an IVUS imaging system.

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the disclosure relates.

FIG. 1 is an illustrative view of device or system 100 useful in internal ultrasound procedures. Such devices may be diagnostic or therapeutic (including interventional) in application, and include devices inserted percutaneously, subcutaneously or endoluminally into the patient. Examples of such devices include embodiments designed for intravascular ultrasound (IVUS) imaging or treatment of deep vein thrombosis (DVT).

Device 100 is usable with an ultrasonic control or analytical (e.g. imaging) system which includes an ultrasound console connected to device 100. The ultrasound console generally includes controls usable by a physician during an ultrasound procedure, and in cases of imaging systems, can include a graphic display which displays graphical images obtained during ultrasound procedures. For example, the ultrasound console can be of a type generally used for medical ultrasonic imaging. Embodiments of device 100 can be used at various locations of a body such as a blood vessel (e.g. IVUS), gastrointestinal tract, urogenital passages (e.g. urethra, ureter, vagina, rectum), throat, nose, ear, or through an artificial opening by percutaneous puncture for example. Device 100 is configured to be used in conjunction with another medical device, such as a catheter, and is capable of emitting and receiving ultrasound signals and then transferring electronic signals (e.g. RF signals) representing the ultrasound signals to the console. The console is configured to extract information from such electronic signals and provides data to the user (e.g. by creating an image viewable on a display). Device 100 when used as an imaging device is configured to create an image of a section of body tissue which may be a two-dimensional slice, a conical slice, or a toriodal-shaped section which is taken from a section which is rotationally symmetric.

The illustrated embodiment of device 100 includes an ultrasound transducer 102 and a reflector 104. Transducer 102 and reflector 104 are indicated schematically in the drawings, positioned within a housing 106. The term "transducer" should be understood to include an assembly of two or more parts as well as a single piece. It will further be understood that "transducer" as used herein includes devices that transmit ultrasound (i.e. transform an electrical (RF) signal to ultrasound), receive ultrasound (i.e. transform ultrasound to an electrical (RF) signal), or both. If multiple transducers or pieces are provided, transmission of ultrasound may occur at one and reception at another. Transducer (s) as described herein may have one or more piezoelectric elements as respective transducers, and may operate in combination with other transducers within or outside the body. As examples, "transducer" as used herein includes a single element transducer on a rotating and pivoting member, a one-dimensional array of elements on a rotating and pivoting member, and a stationary single element transducer generally aimed at a mirror on a rotating and pivoting member. Transducer 102 in a specific embodiment is capable of emitting and receiving ultrasound signals or waves in a range of frequencies which are typically used in therapeutic, imaging or other medical ultrasound procedures, such as, for example, in the range from 20 KHz to 100 MHz.

Figure 2:
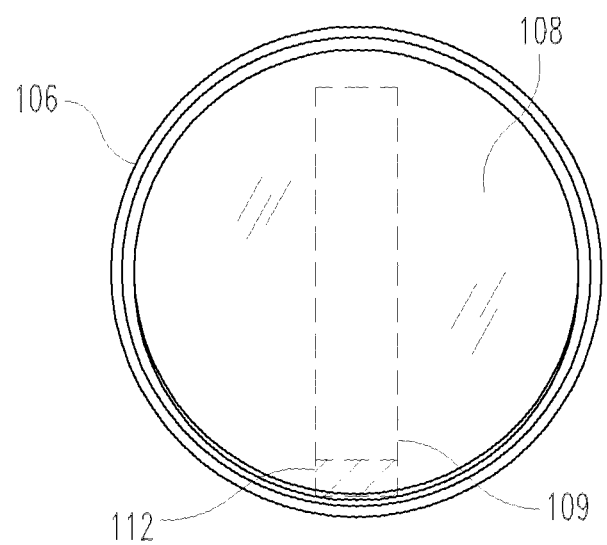
FIG. 2 is a partial cross-sectional illustrative view of the IVUS imaging system of FIG. 1, taken along the line 2-2 in FIG. 1.

The reflector 104 is configured to reflect or otherwise redirect an ultrasound signal from element 102 in a new direction. The reflector 104 can be constructed of any of a variety of materials. The reflector 104 includes a reflection surface 108. The reflection surface 108 is preferably constructed as a smooth surface in order to minimize any scattering of the ultrasound signal that would occur during reflection. In the present example, the reflection surface is an elliptical disc which appears circular when viewed at an angle offset from axis 120 as shown in FIG. 2. The elliptical design could maximize reflection of the ultrasound beam (i.e. reflect the all or a substantial portion of the ultrasound beam) and minimize the distortion of ultrasound beam from transducer 102, providing improved image quality in imaging applications. The reflection surface 108 can be integral to a frame 109 of reflector 104. Alternatively, the reflector 104 can include a structure portion or substrate part of frame 109 which includes a coated surface or layered material comprising the reflection surface 108. For example, the reflection surface 108 could include a metal or mirror material applied to frame 109 of reflector 104 in order to create the reflection surface 108. With that understanding, the reflector 104 can be generally comprised of any of a variety of materials such as metal, ceramic, or a polymer or any other material which provides adequate reflection characteristics due to sufficiently varied acoustic impedance between the reflection surface 108 and the acoustic impedance of the surrounding environment.

In the illustrated embodiment, transducer 102 is oriented so that it emits and receives ultrasound generally along the central longitudinal axis 120 of device 100. In such cases, reflector 104 is arranged so that reflection surface 108 forms an angle of approximately 45 degrees with axis 120. In that configuration, ultrasound waves emitted from ultrasound element 102 along axis 120 will be redirected by reflection surface 108 substantially perpendicularly to axis 120, or along a radius of housing 106. In other embodiments, reflection surface 108 may form a larger angle with respect to axis 120, redirecting waves more distal or forward of reflector 104, or reflection surface 108 may form a smaller angle with respect to axis 120, redirecting waves more proximal or behind reflector 104. In particular, it has been determined that a slightly forward-looking embodiment may be preferred for reducing undesired effects, for example one in which the reflection surface forms an angle of approximately 42 degrees with axis 120.

The housing 106 is configured to contain the ultrasound element 102, the reflector 104 and other components which make up the IVUS imaging system 100. The housing 106 provides structural support for the components of the IVUS imaging system 100. The housing 106 is illustrated in FIG. 1 as a generally cylindrical shape. The housing 106 can be a stand-alone structure for the IVUS imaging system 100 or it can be part of an additional medical device. For example, the housing 106 could be a portion of a catheter which includes the IVUS imaging system 100. The housing 106 is sealed such that it provides protection to the components of the IVUS imaging system 100 from intrusion of unwanted substances, such as, for example blood. The housing 106 is constructed of a material which is relatively echolucent, i.e. providing a small difference in acoustic impedance compared to the working environment. For example, when used within a blood vessel containing body tissues and blood, housing 106 may be constructed of a structurally rigid polymer material such as polymethylpentene (PMP), polyethylene (PE), or acrylonitrile butadiene styrene (ABS), which have acoustic impedances similar to that of body fluids such as blood. At least the portion of housing 106 and/or a catheter wall which serves as an ultrasound window will have optimal transmission of ultrasound when its thickness is approximately a positive integer multiple of ½ of the wavelength corresponding to center frequency of the ultrasound beam.

The immediate interior of device 100 (which includes transducer 102 and reflector 104) can be completely filled with a fluid that presents ultrasound-carrying characteristics that are similar to the fluid outside of chamber 26. In embodiments used for IVUS procedures, the fluid can be a saline solution, mineral oil, castor oil, alcohol, or other substance providing ultrasound characteristics (e.g. acoustic impedance) around reflector 104 similar to those outside housing 106 (e.g. blood in a blood vessel). A port (not shown) may be placed in the wall 24 bounding chamber 26 to allow a user to inject the fluid into housing 106 just prior to use of device 20. One or more seals may be placed in device 20 to separate the fluid from motor 100, discussed below. Saline and/or alcohol have very good acoustic transmission and low viscosity (low friction), but they are corrosive and must be injected or otherwise placed in chamber 26 at the time of use. Oils (e.g. mineral or caster oil) have slightly worse acoustic properties and much higher viscosity (higher friction), but may be placed in chamber 26 well before using device 20. The fluid is lubricious so as to allow rotation of reflector 104 with minimal interference from frictional torque forces acting against reflector 104 during rotation. The similar acoustic impedances of the exterior environment, housing 106, and interior of device 100 provides a pathway for ultrasound signals to travel from transducer 102 to body tissue with minimal signal loss from undesired scattering and absorption. In this way, acoustic matching can be achieved between body fluids, a catheter wall or housing 106, and the medium immediately surrounding ultrasound element 102 and reflector 104. Acoustic matching ensures that minimal signal losses occur when transmitting and receiving ultrasound signals between ultrasound element 102 and body tissue which enhances the clarity of the resulting image.

Device 100 includes a microminiature motor 110 in this embodiment, for example a piezoelectric motor or an electromagnetic motor. The microminiature motor 110 is configured to impart a rotational motion to the reflector 104. Motor 110 is preferably of a small size, such as a diameter in the range from 0.3 mm to 4 mm. An advantage of a piezoelectric motor 110 compared to other motors such as electromagnetic motors is that the efficiency of the piezoelectric motor is independent of size and piezoelectric motor usually has a high torque-to-size ratio.

Microminiature motor 110 includes a stator portion 116 which is fixed to or with respect to housing 106 such that it does not move relative to the housing 106. The motor 110 also includes a rotor portion or shaft 118 which is rotatable relative to the stator portion 116. The rotor portion 118 is concentric relative to the stator portion 116. The motor 110 in this embodiment is capable of using continuous or pulsed ultrasonic vibrations to provide movement of the rotor portion 118 relative to the stator portion 116 such that the rotor portion 118 rotates relative to the stator portion 116.

An arm 112 connects to reflector 104 to provide an extension and support for the reflection surface 108. Arm 112 is fixedly attached to a shaft 114, with shaft 114 being a part of or fixedly attached to rotor portion 118 of motor 110, so that when the rotor portion 118 rotates (i.e. relative to the stator portion 116 and correspondingly to the housing 106), the shaft 114 also rotates relative to the stator portion 116 and the housing 106. In particular embodiments, one or both of shaft 114, 118 are hollow and/or have an irregular (e.g. non-cylindrical) configuration. The shaft 114 is positioned in a concentric arrangement with the rotor portion 118 and the stator portion 116 relative to the axis 120. The arm 112 provides a radial offset so that arm 112 can bypass the ultrasound element 102 while providing that the reflector 104 can rotate coaxially relative to an axis 120. The shaft 114 is generally configured as a cylinder in this embodiment. According to this arrangement, the motor 110 is capable of imparting a rotational motion to the reflector 104 such that the reflector 104 rotates about the axis 120.

Transducer 102 is fixedly supported by a support 122. The support 122 is a generally cylindrical structure which is positioned concentrically relative to the shaft 114 and also relative to the stator portion 116 and the rotor portion 118. In one example, the support 122 is linked to shaft 114 through the use of bearings 124 such that shaft 114 is rotatable around fixed support 122. The support 122 is fixed with respect to the housing 106 and the stator portion 116. The support 122 can be fixed to the housing 106 at a location of device 100 which is not shown in FIG. 1. In this configuration, transducer 102 is held stationary relative to the housing 106 while the reflector 104 is rotatable about the axis 120 relative to transducer 102 and the housing 106. According to this configuration, the support 122 is positioned concentric with the shaft 114, 118 and the motor 110 such that the support 122 is positioned concentrically inward of the motor 110 or alternatively follows a path through a central lumen existing within the motor 110 or rotor shaft 118. The illustrated embodiment of device 100 eliminates the need for and problems associated with a rotating ultrasound transducer. Additionally, the design eliminates the need for an ultrasound array.

Device 100 includes one or more connection wires which are connected to transducer 102 and which run through or along the support 122. Accordingly, the connection wires for transducer 102 also run through the center portion of the microminiature motor 110 in this embodiment. Device 100 also includes one or more wires which connect to the microminiature motor 110 and which provide control signals and/or electric energy to the microminiature motor 110. Connections in this respect may be maintained via slip ring connection(s) and/or capacitative coupler(s).

During operation of device 100, a physician can position device 100 within the patient using a positioning device such as a catheter, sheath or a wire guide, e.g. placed on or in a catheter or sheath or over a wire guide. As previously noted, embodiments of device 100 may be used in any of a number of locations within a patient, including within the vasculature, and examples reflecting use in the vasculature are noted below. Once system 100 is properly positioned in or near the desired area of body tissue (e.g. tissue to be imaged), microminiature motor 110 is powered such that the rotor portion 118 rotates, e.g. at a uniform angular velocity. Correspondingly, the reflector 104 rotates about the axis 120 in the same manner. Transducer 102 is energized through the connection wire which runs partially through the support 122 and continues to the console of the ultrasound system. Transducer 102 transmits an ultrasound signal substantially in an axial direction relative to the support 122 in this embodiment, i.e. substantially parallel to the axis 120. Almost all of the ultrasound signal encounters the reflective surface 108 and is substantially reflected in a direction away from (e.g. perpendicular) to the axis 120 as denoted by reflection direction 126.

The ultrasound signal (e.g. beam or pulse(s)) passes through the housing 106 until it encounters body tissue, plaque, or other material which has acoustic impedance sufficiently different from surrounding environment (e.g. bodily fluids) to form an acoustic impedance boundary, as at a vascular tissue/blood boundary. At such a boundary, the ultrasound signal is at least partially reflected or otherwise at least partially scattered. As an example, a portion of the ultrasound signal is reflected back towards the reflection surface 108. Upon encountering the reflection surface 108, the ultrasound signal is substantially reflected back towards transducer 102. Simultaneously or subsequently transducer 102 continues to transmit further ultrasound signals and the process is repeated, continuously in certain embodiments over a desired period of time.

During this process, the reflector 104 is rotated about the axis 120 such that the reflection surface 108 causes the reflection direction 126 to move in a sweeping direction which takes the form of a slice, cone shape, or toroidal shape. In this manner, while the reflector 104 rotates about the axis 120, transducer 102 is able to emit and receive ultrasound signals sufficient for the ultrasound system to create or analyze data (e.g. an image) of surrounding body tissue. According to the specifics of the ultrasound procedure or the desires of the physician performing the procedure, device 100 can be moved in an axial direction so that multiple two-dimensional images (or other sets of data) are created at different locations. In this way, the two-dimensional data or images can be processed into a three-dimensional data set or image or alternatively the physician can gain a three dimensional conceptional understanding of the physical characteristics of the adjacent body tissue.

In embodiments used for imaging, device 100 facilitates capture of an image which is free from unnecessary artifacts, obstructions or errors within the image. For example, the arrangement of transducer 102 and the reflector 104 (whereby the support 122 is positioned coaxial with the shaft 114) does not require any wires or other echogenic (i.e. prone to scattering) materials to be positioned within or across the reflection direction 126, even as the reflection direction sweeps around the circumference of housing 106. In this way, there are no wires or other echogenic materials which could cause artifacts within the image or block portions of the redirected ultrasound waves, allowing the physician a clear view of the entirety of the image. Additionally, the microminiature motor 110 which is positioned proximal to the rotating reflector 104 allows a uniform angular velocity to be achieved by the reflector 104. This uniform angular velocity results in an ultrasound image which is free from non-uniform rotational defects (NURD) which can otherwise be a problem with the designs using torque cables and relatively remote motors or rotational power sources.

Device 100 is configured to be used with existing medical devices which are designed for percutaneous, intraluminal, or interstitial procedures. For example, device 100 can be used with a variety of commercially available catheters, e.g. positioned on or within a distal portion or end of a catheter depending on the particular configuration. Device 100 can be positioned within an existing lumen within the catheter. Additionally, device 100 could be mounted externally to the catheter using a variety of mounting devices, glues or other types of arrangements, or could be fashioned with a catheter such that the catheter outer diameter is substantially the same as that of housing 106 (e.g., housing 106 substantially forms a part of the catheter or is sandwiched between catheter parts). Embodiments of device 100 can permit a physician to perform procedures (such as placing or moving stents, grafts, balloons or other structures, administering therapeutics, or other tasks) while simultaneously or sequentially imaging body tissue.

Device 100 includes one or more wires which are routed from the portion of device 100 containing transducer 102 and microminiature motor 110 along the length of the catheter or other medical device to the ultrasound control system console. These wires are connected to transducer 102 and the microminiature motor 110 and transfer radio frequency (RF) signals as well as electrical energy to transducer 102 and the microminiature motor 110. In the case of retrofitting a catheter with device 100, the wires can be routed through a dedicated lumen which can be attached externally to the catheter or alternatively could be routed through an existing lumen within the catheter. Additionally, the microminiature motor 110 could be powered by a battery which is located at a distal portion of device 100 (i.e. the end within the patient, distant from the user) near the microminiature motor 110.

Device 100 could also be used for a variety of other medical procedures and with a variety of other medical devices. The versatility of the embodiments described herein allows ultrasound to be used to guide percutaneous therapeutic interventions such as for example placement of embolism coils, stents, filters, grafts, or balloons via IVUS, performance of biopsies, administering therapeutics, etc. Device 100 can be used to locate various anatomical landmarks that will be used to correctly place or guided therapy. Typical landmarks in the vascular context include confluences, bifurcations, side branches, nearby vessels, nearby nerves, the heart, and other tissues adjacent to vessels or other orifices in which transducer 102 is placed. Device 100 can also be used to locate diseased tissue that will be treated or avoided, such as use during a biopsy to provide an image of a needle being deployed into tissue. During a TIPS procedure an image can be produced to allow a physician to watch a needle being placed into the portal vein. For AAA delivery device 100 can allow a physician to place a guide wire into a contralateral leg. Device 100 could also be used to image the location of a deployed implantable device both during and after deployment.

It will be understood by those skilled in the art that the particular type of mounting procedure for device 100 to an existing medical device can include a variety of different types of mounting methods. Accordingly, the particular methods described herein are not indicative of any limiting aspects of the use capabilities of device 100.

Although particular materials were highlighted herein for some components of device 100, those materials are not intended to be limiting of the types of materials which are suitable to be used in device 100. Additionally, where materials were not highlighted, a variety of materials could be used such as certain types of metals, polymers, ceramics or other types of materials which are suitable for use in devices for subcutaneous use as well as in imaging or other ultrasound procedures.

While the disclosure has been illustrated and described in detail in the drawings and foregoing description, the same is to be considered as illustrative and not restrictive in character, it being understood that only particular embodiments have been shown and described and that all changes, equivalents, and modifications that come within the spirit of the claims are desired to be protected. Features particularly described with respect to one embodiment or structure may be used with or incorporated into other embodiments or structures. All publications, patents, and patent applications cited in this specification are herein incorporated by reference as if each individual publication, patent, or patent application were specifically and individually indicated to be incorporated by reference and set forth in its entirety herein. In particular, Application Ser. No. 61/713,135 and filed Oct. 12, 2012; Ser. No. 61/713,172 and filed Oct. 12, 2012; Ser. No. 61/713,142 and filed Oct. 12, 2012, are each incorporated herein by reference in their entireties.

The invention claimed is:

1. A system for use with ultrasound procedures comprising:

a transducer connected to a support for maintaining the transducer in position, the transducer adapted to emit and/or receive ultrasound signals substantially along an axis;

a microminiature motor connected to a shaft and configured to rotate the shaft about the axis;

a reflector connected to the shaft, the reflector positioned with respect to the transducer to reflect the ultrasound signals in a direction non-parallel to the axis, wherein at least the reflector is in a housing, and wherein no echogenic material is both within the housing and within the path of the ultrasound signals; and wherein the shaft and support are positioned concentrically and at least a part of the support is positioned concentrically inward relative to the microminiature motor, so that the shaft is rotatable relative to the support about the axis.

2. The system of claim 1, wherein the housing is around the transducer and the reflector, and wherein the support is fixed in a stationary position relative to the housing.

3. The system of claim 1, further comprising at least one electrical wire connected to the transducer, wherein the reflector is angled with respect to the axis of the transducer so that a reflection direction from the reflector is non-parallel to the axis, and wherein the wire does not cross the reflection direction.

4. The system of claim 3, wherein the reflector forms an angle of between about 10 and 84 degrees with respect to the axis.

5. The system of claim 1, wherein the microminiature motor is a piezoelectric motor.

6. The system of claim 1, wherein the microminiature motor is an electromagnetic motor.

7. The system of claim 1, wherein the microminiature motor, reflector, and transducer are configured to be positioned in a medical device, configured for internal use.

8. The system of claim 7, further comprising one or more electrical wires connected to the transducer and one or more electrical wires connected to the microminiature motor.

9. The system of claim 8, wherein at least one of the one or more electrical wires is housed within the support.

10. The system of claim 1, wherein: the housing contains the reflector and transducer, the housing has a leading end, and the reflector is positioned between the leading end and the transducer.

11. The system of claim 1, wherein the transducer is a single element transducer.

12. The system of claim 1, wherein the transducer, reflector and motor are sized and configured for intravascular usage.

13. The system of claim 1, wherein the transducer has a width dimension non-parallel to the axis and the shaft has a diameter that is smaller than the transducer's width dimension.

14. An internal ultrasound system comprising:
a transducer connected to a support;
a reflector within a housing to reflect a signal from and/or to the transducer, wherein the reflector is connected to a shaft and spaced from the transducer, wherein no echogenic material is both within the housing and within the path of the signal and; and
a microminiature motor connected to the shaft and configured to cause the shaft to rotate;
wherein the microminiature motor, reflector, and transducer are configured to be positioned in a medical device having a leading end and adapted for internal medical use, and wherein the reflector is closer to the leading end than the transducer is to the leading end.

15. The system of claim 14, wherein the microminiature motor is a piezoelectric motor having a size of approximately 0.3 mm to 4 mm.

16. The system of claim 14, wherein the microminiature motor is an electromagnetic motor having a size of approximately 0.3 mm to 4 mm.

17. The system of claim 14, wherein the shaft and support are positioned concentrically and wherein the shaft is rotatable about an axis relative to the support.

18. The system of claim 17, wherein the support is fixed in a stationary position relative to the housing.

19. The system of claim 14, wherein at least a part of the support is positioned concentrically inward relative to the microminiature motor.

20. The system of claim 14, wherein the transducer is a single element transducer.

21. The system of claim 14, further comprising one or more electrical wires connected to the transducer and one or more electrical wires connected to the microminiature motor.

22. The system of claim 21, wherein at least one of the one or more electrical wires is housed within the support.

23. The system of claim 21, wherein the shaft is rotatable about an axis coaxial with the support, wherein the reflector generates a viewing angle approximately perpendicular to the axis, and wherein at each angular position of the reflector the viewing angle does not cross any electrical conductors.

* * * * *